(12) United States Patent
Schafer et al.

(10) Patent No.: US 9,188,696 B2
(45) Date of Patent: Nov. 17, 2015

(54) MITIGATION OF RADIATION LEAKAGE VIA ENTRY PORT AND/OR EXIT PORT OF RADIATION SYSTEM

(71) Applicant: Analogic Corporation, Peabody, MA (US)

(72) Inventors: David Schafer, Rowley, MA (US); Eric Finck, Newton, NH (US)

(73) Assignee: Analogic Corporation, Peabody, MA (US)

( * ) Notice: Subject to any disclaimer, the term of this patent is extended or adjusted under 35 U.S.C. 154(b) by 80 days.

(21) Appl. No.: 13/926,106

(22) Filed: Jun. 25, 2013

(65) Prior Publication Data

US 2014/0376692 A1    Dec. 25, 2014

(51) Int. Cl.
*G01V 5/00* (2006.01)
*G01N 23/04* (2006.01)

(52) U.S. Cl.
CPC .............. *G01V 5/0016* (2013.01); *G01N 23/04* (2013.01); *G01N 23/046* (2013.01); *G01V 5/0008* (2013.01)

(58) Field of Classification Search
CPC ...... A61B 6/032; A61B 6/0471; G01N 23/00; G01N 23/02; G01N 23/04; G01N 23/06; G01N 23/083; G01N 23/10; G01N 23/16; G01N 2223/419
USPC ............. 378/4, 21, 51, 57, 62, 98.8, 203, 208
See application file for complete search history.

(56) References Cited

U.S. PATENT DOCUMENTS

| | | | |
|---|---|---|---|
| 6,542,580 B1* | 4/2003 | Carver et al. | 378/57 |
| 7,151,817 B1* | 12/2006 | Abraham et al. | 378/57 |
| 2007/0230656 A1* | 10/2007 | Lowes et al. | 378/57 |
| 2010/0172464 A1* | 7/2010 | Pavlovich et al. | 378/9 |
| 2011/0142201 A1* | 6/2011 | Eberhard et al. | 378/57 |

OTHER PUBLICATIONS

Mery, Automated detection in complex objects using a tracking algorithm in multiple X-ray views, Jun. 2011, IEEE Computer Society Conference on Computer Vision and Pattern Recognition Workshops (CVPRW), p. 41, 42.*

* cited by examiner

*Primary Examiner* — Irakli Kiknadze
*Assistant Examiner* — Julio M Duarte-Carvajalino
(74) *Attorney, Agent, or Firm* — Cooper Legal Group, LLC

(57) ABSTRACT

Among other things, an object scanner, such as an x-ray system, is provided, where the object scanner is configured to translate an object undergoing an examination along a non-linear path. For example, in some embodiments, an examination region of the object scanner is spatially offset, relative to an entry port and/or an exit port of the object scanner, such that there is little to no line of sight through the object scanner, from the entry port to the exit port. The non-linearity of the path is configured to reduce the possibility of radiation scattered by an object and/or by portions of the object scanner from escaping the examination region and exiting the object scanner via the entry port and/or the exit port.

20 Claims, 8 Drawing Sheets

MITIGATION OF RADIATION LEAKAGE VIA ENTRY PORT AND/OR EXIT PORT OF RADIATION SYSTEM

BACKGROUND

The present application relates to radiation shielding in a radiation system, or more particularly to the mitigation of radiation leakage from a radiation system. It finds particular application in the context of baggage screening, where objects are translated or conveyed through a radiation system to detect threat items, such as guns, knives, explosives, etc. However, it may also find applicability in medical fields and/or industrial fields, where radiation systems are configured to examine and/or image objects.

Today, radiation systems (e.g., also referred to as imaging systems) such as computed tomography (CT) systems, projection systems, and/or line-scanner systems, for example, are useful to provide information regarding interior aspects of an object under examination and/or images of such interior aspects. Generally, the object is exposed to radiation comprising photons (e.g., such as x-rays, gamma rays, etc.), and an image(s) is formed based upon the radiation absorbed and/or attenuated by interior aspects of the object, or rather an amount of photons that is able to pass through the object. Typically, highly dense aspects of the object absorb and/or attenuate more radiation than less dense aspects, and thus an aspect having a higher density, such as a bone or metal, for example, may be apparent when surrounded by less dense aspects, such as muscle or clothing.

In some radiation systems, such as systems commonly found at security checkpoints, an energy shield, such as a lead curtain, is placed at an entry port of the radiation system and/or at an exit port of the radiation system. Such a shield is configured to mitigate radiation leakage to an environment external to the radiation system. Typically, such an energy shield is comprised of a plurality of flaps, and the force of an object (e.g., such as a suitcase) being guided into or out of the radiation system (e.g., via a conveyor belt) causes flaps that contact the object to move, permitting the object to enter the radiation system and be exposed to radiation and/or permitting the object to exit port the radiation system.

SUMMARY

Aspects of the present application address the above matters, and others. According to one aspect, an object scanner configured to examine an object via radiation is provided. The object scanner comprises a first port through which the object enters or exits the object scanner. The object scanner also comprises an examination region through which the object translates in a first direction, the examination region spatially offset relative to the first port in a second direction substantially perpendicular to the first direction such that there is no linear path parallel to the first direction between the examination region and the first port.

According to another aspect, an object scanner configured to examine an object via radiation is provided. The object scanner comprises an entry port through which the object enters the object scanner and an exit port through which the object exits the object scanner. The object scanner also comprises an examination region through which radiation is transmitted. The examination region is situated between the entry port and the exit port. The object scanner further comprises a translator configured to translate the object along a non-linear path between the entry port and the exit port.

According to another aspect, a method of examining an object is provided. The method comprises translating the object along a non-linear path between an entry port and an exit port of an object scanner and examining the object via radiation while the object is within an examination region situated between the entry port and the exit port. The non-linear path inhibits radiation from passing linearly from the examination region to at least one of the entry port or the exit port.

Those of ordinary skill in the art may appreciate still other aspects of the present application upon reading and understanding the appended description.

FIGURES

The application is illustrated by way of example and not limitation in the figures of the accompanying drawings, in which like references generally indicate like elements and in which.

DESCRIPTION

Figure 1:
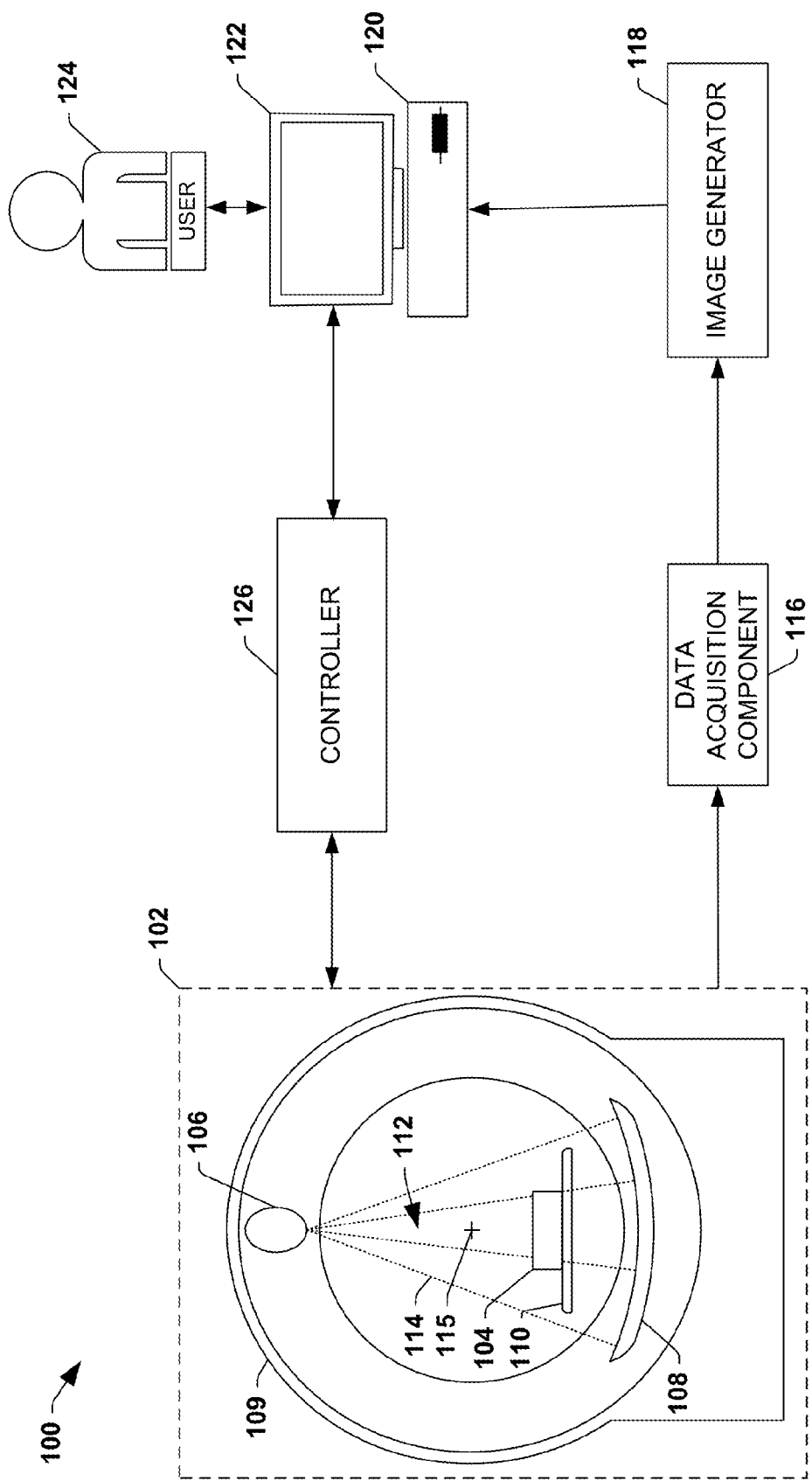
FIG. 1 is a schematic block diagram illustrating at least some of an example object scanner.

The claimed subject matter is now described with reference to the drawings, wherein like reference numerals are generally used to refer to like elements throughout. In the following description, for purposes of explanation, numerous specific details are set forth in order to provide an understanding of the claimed subject matter. It may be evident, however, that the claimed subject matter may be practiced without these specific details. In other instances, structures and devices are illustrated in block diagram form in order to facilitate describing the claimed subject matter.

For purposes of the instant application, the z-direction is intended to refer to a direction that an object is translated through an examination region of a radiation system. In CT systems, where a rotating gantry comprising a radiation source and/or a detector array is configured for at least partial rotation about an object during an examination, an axis of rotation may extend in the z-direction. Accordingly, the radiation source and/or detector array may rotate in an x,y plane. In line-scanner systems and/or digital projection systems, where the radiation source and detector array are substantially fixed in position during an examination, a line perpendicular to the detector array and extending toward the radiation source may extend in the y-direction (e.g., perpendicular to the z-direction). The x-direction is substantially perpendicular to the y-direction and the z-direction. Typically, when viewing a radiation system in a security application, the y-axis extends vertically from a floor of a room within which the radiation system is situated, the z-axis extends perpendicularly to the y-axis and parallel to a direction that a conveyor conveys objects through the examination region of the radiation system, and the x-axis extends perpendicularly to the y-axis and to the z-axis.

Baggage systems at airports and/or other security checkpoints typically comprise a conveyor belt that is configured to convey bags or other objects through the radiation system. The object is typically loaded onto the conveyor belt upstream of the radiation system and conveyed into the radiation system at an entry port of the radiation system, located on an upstream side of an examination region of the radiation system. While within the radiation system, the object is conveyed into the examination region, where the object is exposed to radiation. When the examination is complete, the object is output from the radiation system at an exit port, typically located on a downstream side of the radiation system. A span of the radiation system that the bag travels between the entry port and the exit port may be referred to as a tunnel.

Conventionally, the entry port, examination region, and exit port have been substantially collinear (e.g., a line drawn from the entry port to the exit port would intersect the examination region) and the object has been translated substantially linearly within the radiation system. That is, conventional radiation systems have been configured such that there is a direct line-of-sight from the entry port to the exit port (e.g., a user peering into the entry port could see through to the exit port if lead curtains or other shielding material were removed from the tunnel).

To mitigate radiation leakage at the entry port and/or exit port of the radiation system, energy shields (e.g., lead curtains or doors) are typically positioned within the tunnel proximate the entry port and/or the exit port. Such energy shields are configured to attenuate radiation that escapes the examination region and/or to inhibit radiation from exiting the radiation system. While such an approach is generally successful at mitigating radiation leakage when the radiation system experiences low throughput, at peak hours when the radiation system may experience higher throughput, the energy shields may be opened a greater degree and/or for a greater duration to allow objects to pass through, thereby potentially allowing radiation to be emitted from the radiation system. Further, as described above, such energy shields may create jams within the radiation system.

Additional and/or supplemental approaches for mitigating radiation leakage at an entry port and/or an exit port of a radiation system, such as a line-scanner system, digital projection system, and/or CT system, for example, are provided for herein. More particularly, the examination region is spatially offset relative to the entry port and/or the exit port, such that the examination region is not collinear with at least one of the entry port or the exit port. For example, the examination region may be offset in at least one of an x-direction or a y-direction such that a direct line-of-sight from the entry port to the exit port, passing through the examination region, is at least partially obstructed.

In some embodiments, the radiation system is configured such that the object is translated (e.g., conveyed) along a non-linear path between the entry port and the exit port. For example, an object being translated may experience a turn between the entry port and the examination region and/or between the examination region and the exit port. As another example, the object may experience a substantially vertical drop or increase in elevation between the entry port and the examination region and/or between the examination region and the exit port. It may be appreciated that the term first port and/or second port may, at times, be used herein to refer to either the entry port or the exit port. That is, first port may refer to the entry port and/or the exit port. Similarly, second port may refer to the entry port and/or the exit port.

In some embodiments, the examination region is spatially offset relative to the entry port and/or the exit port such that there is no linear path between the examination region and at least one of the entry port or the exit port (e.g., through which radiation could travel between the examination region and the entry port and/or the exit port without intersecting, impinging, etc. an interior surface of the radiation system defining the tunnel). That is, stated differently, the examination region is offset in at least one of an x-direction or a y-direction to such an extent that there is no linear path (e.g., in any direction) between the examination region and at least one of the entry port or the exit port (e.g., there is no linear path in any direction from any point in the examination region to any point in the entry port and/or the exit port). In this way, there is no linear path for radiation to travel between the examination region and the entry port and/or between the examination region and the exit port (e.g., reducing an amount of secondary radiation that reaches the entry port and/or the exit port), for example. In still other embodiments, the examination region may be offset in at least one of an x-direction and/or a y-direction to such an extent that at least 50%, or other desired percentage/measurement, of the radiation escaping the examination region would intersect, impinge, etc. an interior surface of the radiation system defining the tunnel (e.g., thus reducing scattered emission and/or reducing the amount of shielding required proximate the entry port and/or the exit port). That is, stated differently, the degree to which the examination region is offset relative to the entry port and/or the exit port may depend upon a desired reduction in radiation emissions (e.g., relative to radiation emissions emitted in a configuration where the examination region and at least one of the entry port or the exit port are in-line with one another such as to provide a unobstructed, direct line of sight between the examination region and at least one of the entry port or the exit port).

Turning to FIG. 1, an example object scanner 100 configured to examine objects via radiation is illustrated. In the example illustrated, the object scanner 100 comprises a radiation system that functions as a CT system configured to view an object 104 from multiple angles by rotating at least one of a radiation source 106 and/or a detector array 108 relative to the object 104. It will be appreciated that while specific reference is made herein to a CT system, features and/or techniques described herein may find applicability to other types of radiation systems, such as line-scanner systems, digital projection systems, etc., where an object is translated into an examination region 112 and examined via radiation 114. Moreover, the following description is not intended to be interpreted in a limiting manner, such as necessarily specifying the location, inclusion, and/or relative arrangement of the components depicted therein. By way of example, a data acquisition component 116 as illustrated in FIG. 1 may be part of a detector array 108, for example.

In the example illustrated, an object examination apparatus 102 of the object scanner 100 is configured to examine one or more objects 104 (e.g., a series of suitcases at an airport, a human patient, etc.). A cross-section of the object examination apparatus 102 is illustrated and comprises one or more radiation sources 106 (e.g., an x-ray source, gamma-ray source, or other ionizing radiation source) and a detector array 108 mounted on a diametrically opposite side of the object examination apparatus 102 relative to the radiation source(s) 106. The radiation source(s) 106, detector array 108, and/or examination region 112 may be substantially enclosed by a housing 109. In some embodiments, the housing 109 comprises one or more radiation shields, such as lead panels, configured to mitigate radiation leakage from the object examination apparatus 102 to an environment external to the object examination apparatus 102.

A translator 110 (e.g., a conveyor belt, series of rollers, etc.) is configured to support the object(s) 104 and/or translate the object(s) 104 through the object examination apparatus 102. By way of example, objects 104 to be examined may be loaded into the object examination apparatus 102 at an entry port and translated into an examination region 112, some distance away from the entry port, where the objects 104 are exposed to radiation 114. After the examination, the objects 104 may be translated to an exit port of the object examination apparatus 102, some distance away from the examination region 112, where users can then, once again, interact with the objects 104. Typically, a span of the object examination apparatus 102 between the entry port and the exit port is enclosed by the housing 109.

During an examination, the radiation source(s) 106 is configured to emit fan, cone, wedge, and/or other shaped radiation configurations into the examination region 112 of the object examination apparatus 102. It may be appreciated that such radiation 114 may be emitted substantially continuously and/or may be emitted intermittently (e.g., a short pulse of radiation 114 is emitted followed by a resting period during which the radiation source(s) 106 is not activated). Moreover, the radiation 114 may be emitted at a single spectrum or multiple, distinct energy spectrums (e.g., such as may occur where the radiation system 100 is a dual-energy system).

In CT systems, such as illustrated, the radiation source(s) 106 and/or the detector array 108 may be mounted to a rotating gantry configured to rotate about the object(s) 104. In such systems, an axis of rotation 115 is generally defined as extending in the z-direction (e.g., into and out of the page) and the rotating gantry is configured to rotate in an x,y plane (e.g., parallel to a plane of the page). Further, objects 104 may be translated through the examination region 112 in a direction substantially parallel to the axis of rotation 115. Thus, objects 104 are typically translated in the z-direction while the rotating gantry is rotating in an x,y plane causing the object to be examined helically, for example.

As the emitted radiation 114 traverses the object(s) 104, the radiation 114 may be attenuated differently by different aspects of the object(s) 104. Because different aspects attenuate different percentages of the radiation 114, an image(s) may be generated based upon the attenuation, or variations in the number of radiation photons that are detected by the detector array 108. For example, more dense aspects of the object(s) 104, such as a bone or metal plate, may attenuate more of the radiation 114 (e.g., causing fewer photons to be detected by the detector array 108) than less dense aspects, such as skin or clothing. It is to be appreciated that attenuation may comprise absorption and/or scattering of at least some of the radiation 114. The scattering of radiation by the object and/or by aspects of the object examination apparatus (e.g., such as anti-scatter plates, the translator, etc.) may cause some of the radiation to exit the examination region 112 (e.g., such as along a pathway object(s) followed into or out of the examination region 112).

The detector array 108 is configured to directly convert and/or indirectly convert detected radiation into analog signals that can be transmitted from the detector array 108 to a data acquisition component 116 configured to convert analog signals output by the detector array 108 into digital signals and/or to compile signals that were transmitted within a predetermined time interval, or measurement interval, using various techniques (e.g., integration, photon counting, etc.). Such digital signals and/or compiled signals may be referred to as projection data because the data is typically in projection space (e.g., although depending upon the type of radiation system, for example, such data may be in image space).

In the example environment, an image generator 118 is configured to receive the projection data that is output by the data acquisition component 116. Such an image generator 118 may be configured to generate image data from the projection data using a suitable analytical, iterative, and/or other image generation technique (e.g., backprojection reconstruction, tomosynthesis reconstruction, iterative reconstruction, etc.). In this way, the data is converted from projection space to image space, a domain that may be more understandable by a user 124 viewing the image(s), for example. It may be appreciated that in other embodiments, where the data output by the data acquisition component 116 is in image space, an object scanner may not comprise an image generator 118 as provided in the example environment, for example.

The object scanner 100 also includes a terminal 120, or workstation (e.g., a computer), configured to receive the image(s), which can be displayed on a monitor 122 to a user 124 (e.g., security personnel, medical personnel, etc.). In this way, the user 124 can inspect the image(s) to identify areas of interest within the object(s) 104. The terminal 120 can also be configured to receive user input which can direct operations of the object examination apparatus 102 (e.g., a speed of translation, a desired tube current for the radiation source(s) 106, desired tube voltage for the radiation source(s) 106, etc.).

A controller 126 is operably coupled to the terminal 120. In one example, the controller 126 is configured to receive input from the terminal 120, such as user input for example, and to generate instructions for the object examination apparatus 102 indicative of operations to be performed. For example, the user 124 may desire to reexamine the object(s) 104 at a different energy spectrum, and the controller 126 may issue a command instructing the translator 110 to reverse direction (e.g., bringing an object 104 back into the examination region 112 of the object examination apparatus 102).

It may be appreciated that the example object scanner 100 is merely intended to describe an example arrangement of an example radiation system, and other arrangements which comprise at least some of the foregoing components and/or which comprise different components are also contemplated. For example, in another embodiment, the object scanner 100 may comprise a threat detection component configured to receive the projection data from the data acquisition component 116 and/or image data from the image generator 118 and to provide (e.g., automated) threat analysis based upon the projection data and/or image data. Thus, the scope of the disclosure, including the scope of the claims, is not intended to be limited by the foregoing example.

Figure 2:
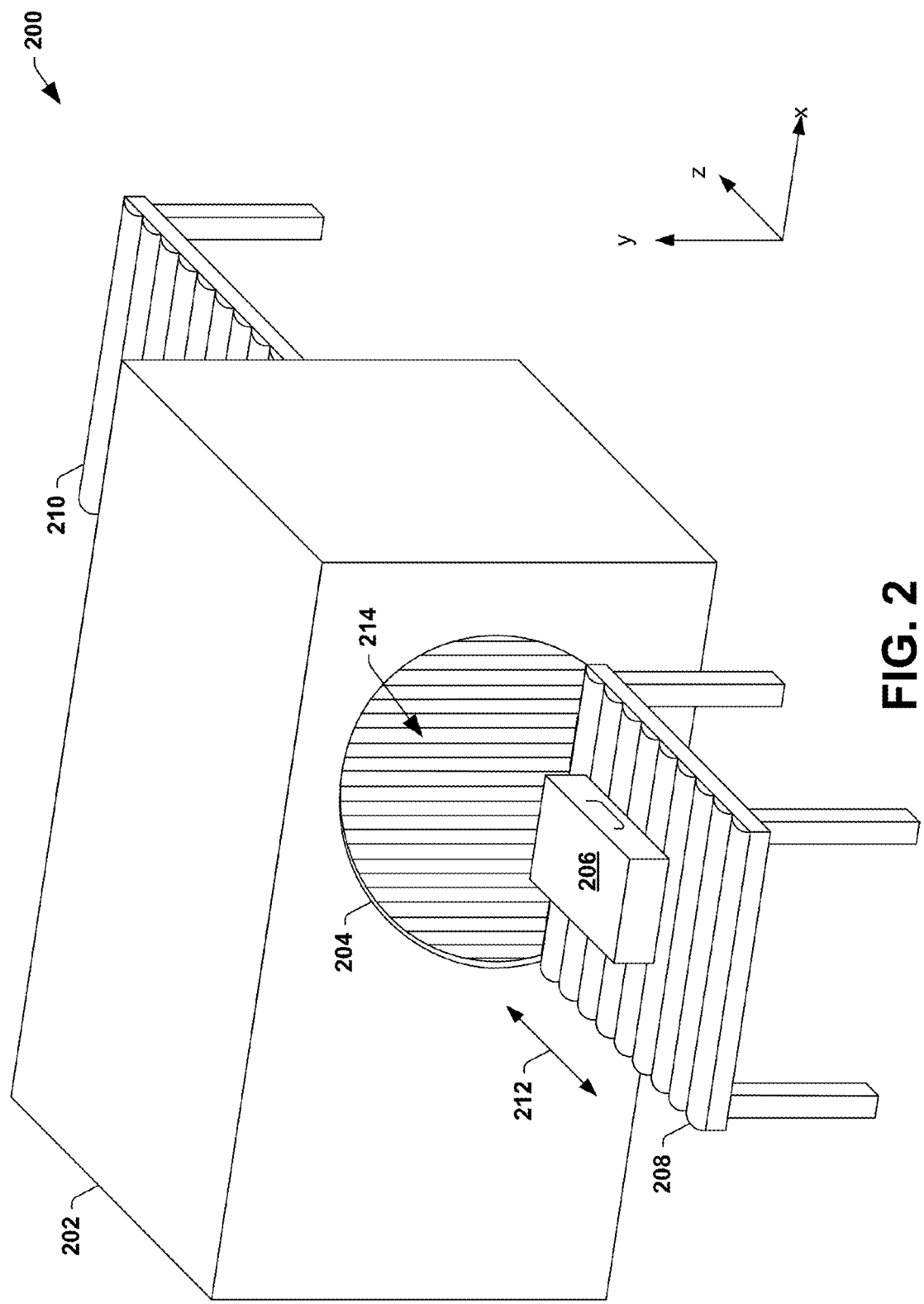
FIG. 2 illustrates an exterior view of at least some of an example object scanner.

FIG. 2 illustrates an external view of an example object scanner 200 (e.g., 100 in FIG. 1) configured to examine and/or image an object utilizing radiation. A radiation source (e.g., 106 in FIG. 1), detector array (e.g., 108 in FIG. 1), and examination region (e.g., 112 in FIG. 1) are enclosed within a housing 202 (e.g., 109 in FIG. 1), and thus may be concealed from view.

The housing 202 generally defines an entry port 204 (e.g., a first bore) via which objects 206 (e.g., 104 in FIG. 1) enter the object scanner 200 and an exit port (e.g., a second bore) via which objects 206 exit port the object scanner 200. Although concealed from view, a translator (e.g., 110 in FIG. 1) is typically configured to convey the objects 206 between the entry port 204 and the exit port. In some embodiments, the exit port is positioned on a diametrically opposite side of the housing 202 relative to the entry port 204.

In the illustrated embodiment, a first conveyor 208 is positioned spatially proximate the entry port 204 and is configured to convey objects 206 through the entry port 204 (e.g., where the objects 206 continue to be conveyed via the translator). A second conveyor 210 may be positioned spatially proximate the exit port and may be configured to receive objects 206 exiting the object scanner 200. In this way, objects may be translated in the z-direction from an area upstream of the entry port 204 to an area downstream of the exit port, for example.

An examination region (e.g., 112 in FIG. 1), within which radiation (e.g., 114 in FIG. 1) is emitted to examine the objects 206, may be located within the object scanner 200. To reduce an amount of radiation exiting the housing 202 (e.g., to mitigate radiation leakage from the object scanner 200) via the entry port 204 and/or the exit port, for example, one or more energy shields 214 may be physically coupled to the housing 202 and may extend into at least one of the entry port 204 or the exit port, or rather into at least some of a tunnel defined between the entry port and the exit port, for example. An energy shield 214 is generally comprised of one or more materials configured to attenuate radiation. For example, an energy shield 214 may by comprised of, but is not limited to, bismuth, barium, lead, tungsten, antimony, copper tin, aluminum, iron, iodine, cadmium, mercury, silver, nickel, zinc, thallium, tantalum, tellurium, and/or uranium.

In some embodiments, an energy shield 214 includes one or more flaps (e.g., extending substantially vertically in the example illustrated) which may be separated from one another via small gaps (e.g., also extending in a substantially vertical direction) to allow adjacent flaps to move relative to one another to allow entry of the object 206 into the object scanner and/or to allow an exit port of the object 206 from the object scanner, for example. In other embodiments, the energy shield 214 may be a substantially one-piece structure which is hinged to the entry port 204 and/or the exit port and may be swung open (e.g., via an actuator) to facilitate entry of an object 206 into the object scanner and/or to facilitate exit of the object 206 from the object scanner, for example.

As provided herein, an internal structure or layout of the object scanner 200 further reduces radiation leakage at the entry port 204 and/or the exit port. For example, the layout of the object scanner 200 may be such that the examination region is spatially offset, relative to the entry port 204 and/or the exit port, in at least one of an x-direction and/or a y-direction. In some embodiments, the examination region may be spatially offset such that there is no direct line-of-sight between the entry port 204 and the exit port that also passes through the examination region. In this way, in some embodiments, there is no linear path for secondary radiation (e.g., scattered by the object 206 and/or by portions of the object scanner 200) to travel between the examination region and the entry port 204 and/or between the examination region and the exit port. In some embodiments, the layout of the object scanner 200 (e.g., or more particularly the location of the examination region relative to the entry port 204 and/or exit port) may mitigate radiation leakage to such an extent that little to no energy shield 214 may be required at the entry port 204 and/or exit port to meet a desired radiation leakage threshold. Moreover, the location of the examination region relative to the entry port and/or the exit port may allow a footprint or size of the object scanner 200 to be reduced (e.g., distance from entry port to exit port may be shortened), where requiring a smaller amount of area may be desirable (e.g., to reduce rental costs).

FIGS. 3-6 illustrate internal views of example layouts of an object scanner having an examination region (e.g., 112 in FIG. 1) that is spatially offset in at least one of the x-direction or the y-direction relative to the entry port and the exit port. In other examples, the examination region may be spatially offset in the x-direction and/or the y-direction relative to merely one of the entry port and the exit port. For example, there may be a direct line-of-sight from the exit port through the examination region, but the entry port may not be visible and/or vice-versa.

Figure 3:
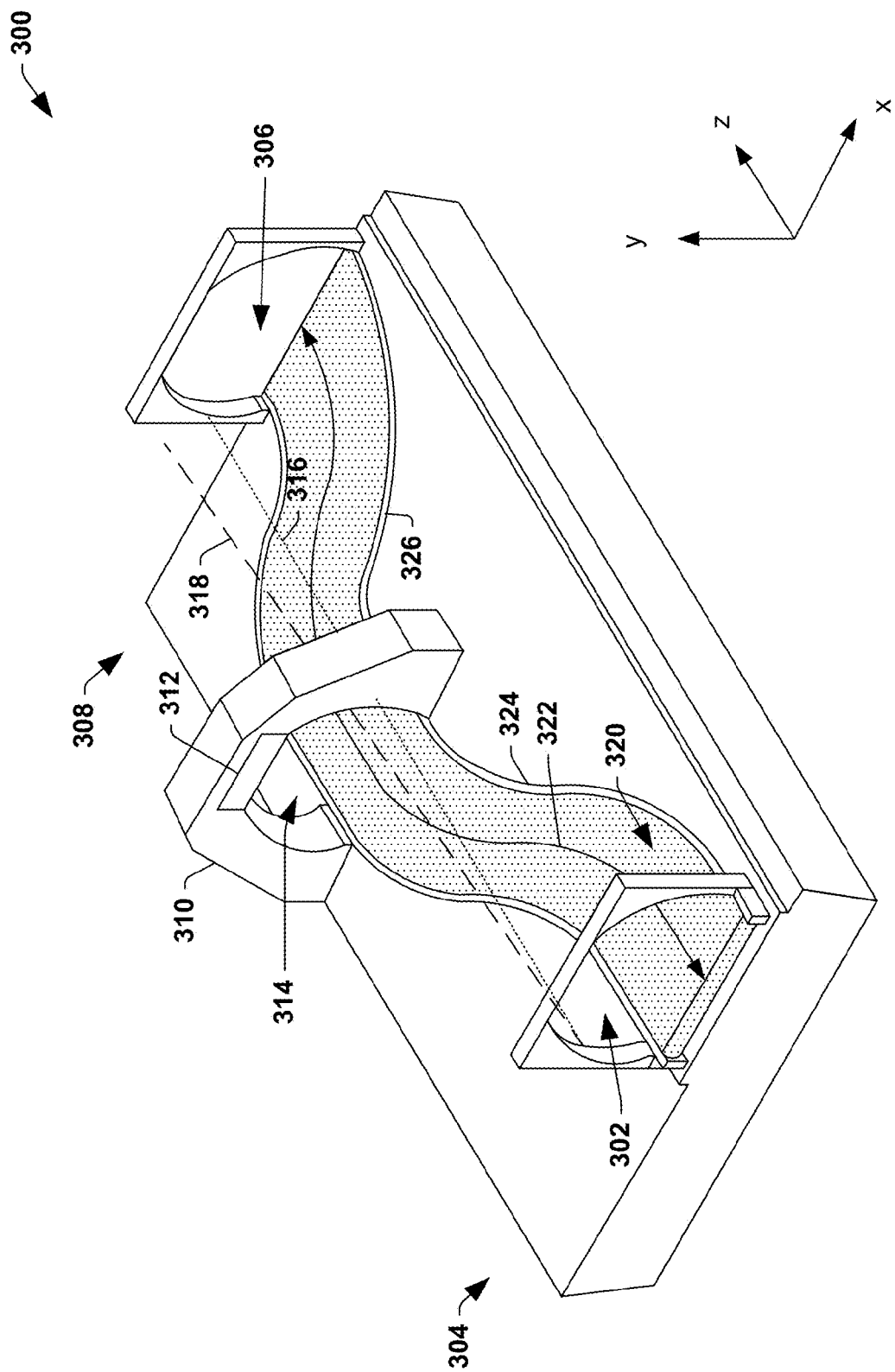
FIG. 3 illustrates an internal view of at least some of an example object scanner.

With respect to FIG. 3, an internal view of an example object scanner 300 (e.g., 200 in FIG. 2) having a first layout is provided. An entry port 302 (e.g., 204 in FIG. 2) is located in an upstream portion 304 of the object scanner 300 and an exit port 306 is located in a downstream portion 308 of the object scanner 300. An examination feature 310 is located, in the z-direction, between the entry port 302 and the exit port 306.

The examination feature 310 is spatially offset in the x-direction relative to the entry port 302 and the exit port 306 and comprises a radiation source 312 (e.g., 106 in FIG. 1) and a detector array (e.g., 108 in FIG. 1). In some embodiments, where the examination feature 310 is configured to rotate about an axis of rotation (e.g., such as where the examination feature 310 is a rotating gantry configured to rotate the radiation source 312 and/or detector array relative to an object under examination), the examination feature 310 may be spatially offset from the entry port 302 and the exit port 306 such that the axis of rotation does not pass through at least one of the entry port 302 or the exit port 306.

A volume of space between the radiation source 312 and the detector array is generally defined as the examination region 314, and thus by spatially offsetting the examination feature 310 in the x-direction relative to the entry port 302 and the exit port 306, the examination region 314 is also spatially offset in the x-direction relative to the entry port 302 and the exit port 306. In some embodiments, the volume of the examination region 314 is substantially equal to the distance between the radiation source 312 and the detector array multiplied by a surface area of the detector array.

As an example, in a CT system, the examination feature 310 may be a rotating gantry configured to rotate the radiation source 312 and the detector array about an object under examination. In such an embodiment, the examination feature 310 may be shaped to define a substantially cylindrical bore through which the object is translated during the examination, and the volume of the examination region 314 may be substantially equal to a cross-sectional or substantially circular area of the bore multiplied by a length of the detector array in the z-direction. Further, a circumference of the bore may define an outer perimeter of the examination region 314, for example.

In the illustrated embodiment, the examination region 314 is spatially offset in the x-direction relative to the entry port 302 and the exit port 306 such that there is no direct line-of-sight, from the entry port 302 to the exit port 306 that also extends through the examination region 314. That is, stated differently, no linear line can be drawn between the entry port 304 and the exit port 306 that intersects the examination region 306. For example, a dotted line 316 is drawn in FIG. 3 from a point of the entry port 302 spatially nearest the examination region 306 in the x-direction to a point of the exit port 306 spatially nearest the examination region 306 in the x-direction. As illustrated, the dotted line 316 intersects the examination feature 310 (e.g., the rotating gantry) but does not pass through the examination region 314. Thus, no linear line arbitrarily drawn from the entry port 302 to the exit port 306 will intersect the examination region 314.

As another technique for showing there is no direct line-of-sight, no linear line can be drawn through the examination region 314 that also passes through both the entry port 302 and the exit port 306. For example, a dashed line 318 is drawn in FIG. 3 from the point of the entry port 302 spatially nearest the examination region 314 through an edge of the examination region 314 spatially nearest the exit port 306. As illustrated, the dashed line 318 does not intersect the exit port 306 and thus no linear line arbitrarily drawn from the entry port 302 through the examination region 314 will intersect the exit port 306. While not shown, a similar procedure can be performed to confirm that no line drawn from the exit port 306 and extending through the examination region 314 will intersect the entry port 302.

A translator 320 of the object scanner 300 is configured to translate objects between the entry port 302 and the exit port 306 and through the examination region 314. Such a translator 320 may comprise one or more of a conveyor belt, power rollers, gravity-fed rollers, electro-magnetic propulsion system, and/or other electro/mechanical devices configured to move objects, such as baggage, along a predetermined path 322 between the entry port 302 and the exit port 306 (e.g., from an upstream portion 304 of the object scanner 300 to a downstream portion 308).

Due to the examination region 314 being spatially offset from the entry port 302 and the exit port 306 in the x-direction, the path 322 along which the object is translated by the translator 320 is non-linear. By way of example, in the illustrated embodiment, the translator 320 is configured such that objects, translated by the translator 320, experience a first turn 324 between the entry port 302 and the examination region 314 and experience a second turn 326 between the examination region 314 and the exit port 306. Thus, the translator 320 is configured to, at times, translate objects along a trajectory having both a z-component and the x-component, for example. At other times, the object may be translated along a trajectory having merely an x-component or a z-component. By way of example, in may be desirable in some applications for the translator 320 to translate objects through the examination region 314 in a direction substantially parallel to an axis of rotation of the examination feature 314. Accordingly, the translator 320 may be configured to translate the objects through the examination region 314 substantially in the z-direction.

Although not shown, in some embodiments, one or more energy shields may be positioned along the path between the entry port 302 and the exit port 306. For example, a first energy shield may be positioned at the entry port 302 of the object scanner 300 and a second energy shield may be positioned within the first turn 324. As another example, a first energy shield may be positioned along a portion of the path 322 proximate the entry port 302 and a second energy shield may be positioned along a portion of the path proximate the examination region 314. It may be appreciated that any number of energy shields may be located at any one or more positions, however. Also, the examination region 314 may be offset from merely the entry port 302 or the exit port 306, but not necessarily both.

Figure 4:
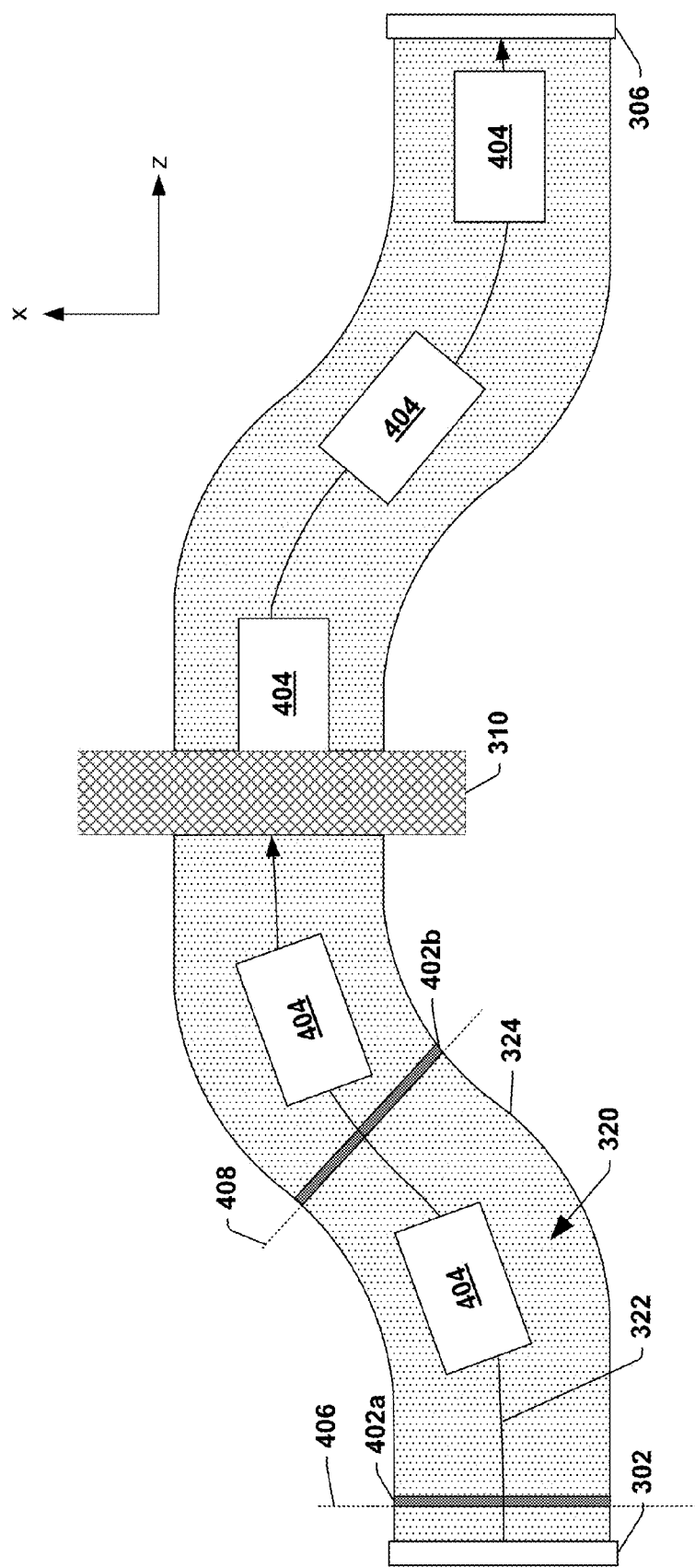
FIG. 4 illustrates an internal view of at least some of an example object scanner.

Turning to FIG. 4, a second internal view (e.g., top-down view) of the example object scanner 300 is provided. The second view illustrates, among other things, the placement of one or more energy shields 402 as well as the position of an object 404 at various points along the path 322 over which a translator 320 translates the object 404. By way of example, the object 404 may enter the object scanner 300 at the entry port 302 and be translated along the path in a non-linear manner from the entry port 302, through the examination feature 310, and to the exit port 306.

During the translation, the object 404 may encounter energy shields 402, such as a first energy shield 402a and a second energy shield 402b. In some embodiments, a contacting face of the first energy shield 402a (e.g., a face of the first energy shield 402a which contacts the object 404 while the object is being translated from the entry port 302 to the exit port 306) is not parallel with a contacting face of the second energy shield 402b. For example, the contacting face of the first energy shield 402a may lay within a plane illustrated by a first dashed line 406 (e.g., and extending into and out of the page) and the contacting face of the second energy shield 402b may lay within a plane illustrated by a second dashed line 408 (e.g., and extending into and out of the page), which is not parallel to the first dashed line 406. Such positioning of the first energy shield 402a relative to the second energy shield 402b may further inhibit radiation from escaping through the entry port (e.g., because slits or gaps between vertical flaps of the first energy shield 402a are not aligned with gaps between vertical flaps of the second energy shield 402b linear pathways through which radiation can travel are reduced). It may be appreciated that while FIG. 4 merely illustrates energy shields 402 between the entry port and the examination feature 310, energy shields may also or instead be placed between the examination feature 310 and the exit port 306.

Figure 5:
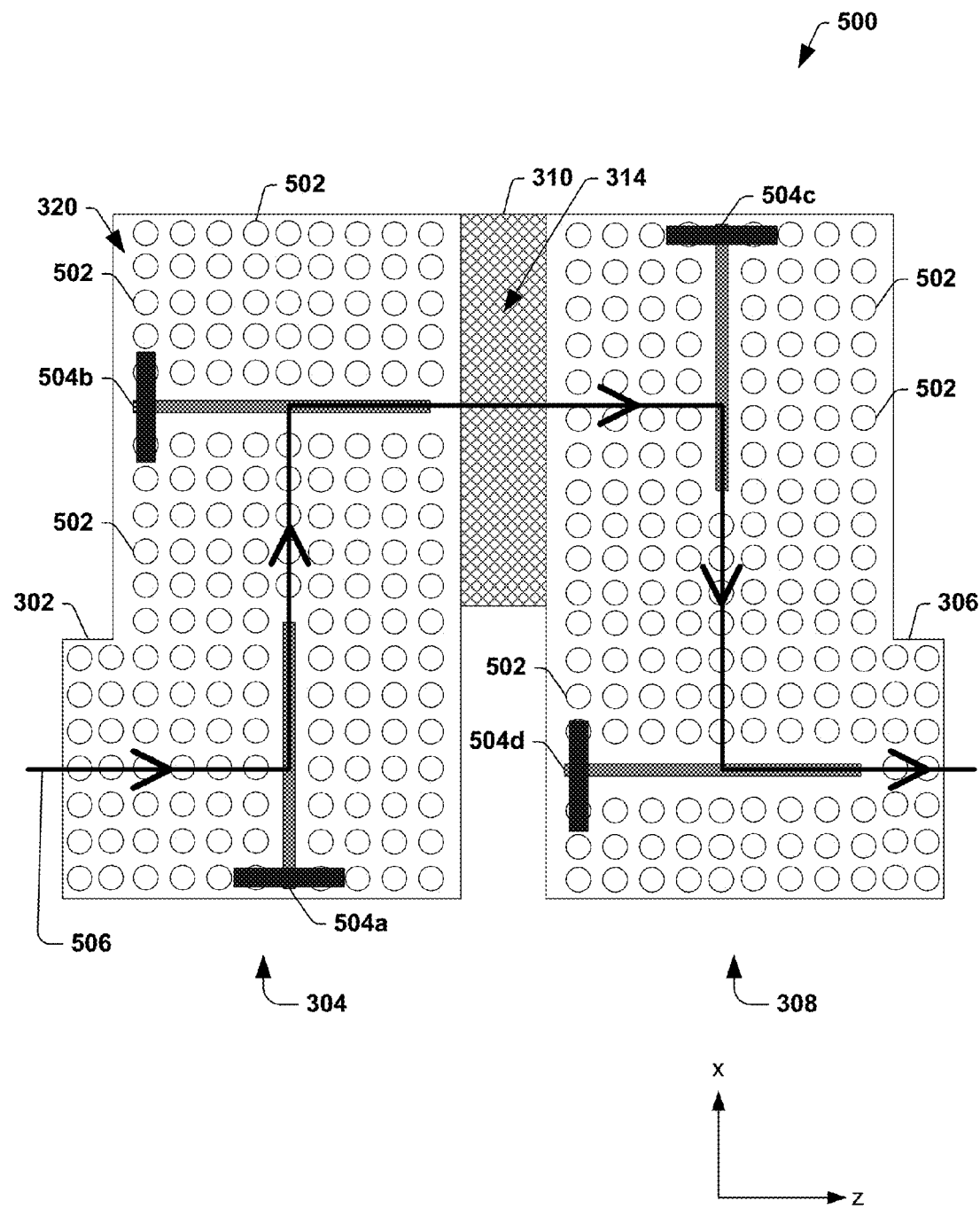
FIG. 5 illustrates an internal view of at least some of an example object scanner.

Turning to FIG. 5, an internal view (e.g., a top-down view) of an example object scanner 500 (e.g., 300 in FIG. 3) having a second layout is provided. Similar to the layout shown in FIGS. 3-4, the entry port 302 is located in an upstream portion 304 of the object scanner 500 and an exit port 306 is located in a downstream portion 308 of the object scanner 500. An examination feature 310 is located between the entry port 302 and the exit port 306 in the z-direction and is spatially offset from the entry port 302 and the exit port 306 in the x-direction. Accordingly, an examination region 314 (e.g., defined at least in part by the examination feature 310) is also spatially offset from the entry port 302 and the exit port 306 in the x-direction.

A translator 320, which in the illustrated embodiment comprises a plurality of rollers 502 (e.g., ball bearings) and actuators 504, is configured to translate objects along a substantially u-shaped path 506 which extends from the entry port 302 to the exit port 306 and passes through the examination region 314 and/or through a bore in the examination feature 310, for example. By way of example, an object may be conveyed through the entry port 302 of the object scanner 500 via a first conveyor (e.g., 208 in FIG. 2), and the presence and/or position of the object inside the object scanner 500 may be detected by one position sensors, for example. Upon the position sensor detecting the presence of an object, the position sensor may transmit a signal which activates a first actuator 504a (e.g., a linear actuator) configured to propel the object linearly in the x-direction to align the object with an entry port of the examination region 314 (e.g., and/or to align the object with a bore through the examination feature 310). Once aligned with an entry port of the examination region 314, a second actuator 504b may be configured to propel the object linearly in the z-direction to convey the object through the examination region 314, where the object is examined via radiation. Upon exiting the examination region 314, a third actuator 504c may be configured to propel the object linearly in the x-direction to align the object with the exit port 306 of the object scanner 500, where a fourth actuator 504d may propel the object through the exit port 306. It may be appreciated that while specific reference is made herein the use of rollers 502 and actuators 504 to translate the object along the u-shaped path 506, one or more other mechanisms for translating an object, such as a conveyor belt, power rollers, electro-magnetic propulsion systems, etc. may also or instead be used to convey objects along such a path.

Moreover, in contrast to FIGS. 3-4 where an object is described as being translated, at times, along a trajectory having both an x-component and a z-component, the trajectory of an object along the path 506 illustrated in FIG. 5 generally has merely has a x-component or a z-component (e.g., and not both) at any given point in time (e.g., but might have a slight x-component when travelling primarily in the z-direction and/or might have a slight z-component when travelling primarily in the x-direction). Thus, the object is, at times, translated at 90 degree angles between the entry port 302 and the exit port 306, for example.

While FIGS. 3-5 illustrate spatially offsetting the examination feature 310 and/or the examination region 314 relative to the entry port 302 and the exit port 306 in the x-direction, in some embodiments, the examination feature 310 and/or examination region 314 may be spatially offset relative to the entry port 302 and/or the exit port 306 in the y-direction (e.g., instead of or in addition to the offset in the x-direction) to at least partially obstruct a direct line-of-sight from the entry port 302, through the examination region 314, to the exit port 306. By way of example, FIG. 6 illustrates an example embodiment where the examination feature 310 and examination region 314 are spatially offset relative to the entry port 302 and the exit port 306 in the y-direction and objects are translated along a non-linear path 602 that includes a z-component and a y-component.

The entry port 302 and the exit port 306 are positioned at a first elevation 604 relative to a floor 606 of an examination room comprising the object scanner 600 and the examination region 314 is positioned at a second elevation 608 relative to the floor 606. Accordingly, an object 610 entering the object scanner 600 via the entry port 302 experiences a substantially vertical drop in elevation between the entry port 302 and the examination region 314 and may experience a substantially vertical increase in elevation between the examination region 314 and the exit port 306. By way of example, in some embodiments, a translator comprises one or more conveyor belts 612 configured to convey the object 610 in the z-direction and one or more lift mechanisms 614 configured to convey the object 610 in the y-direction. For example, a first lift mechanism 614a (e.g., a first elevator) may be configured to lower the object 610 from the first elevation 604 of the entry port 302 to the second elevation 608 of the examination region 314 and a second lift mechanism 614b may be configured to raise the object from the second elevation 608 of the examination region 314 to the first elevation 604 of the exit port 306.

In the illustrated embodiment, the examination region 314 is spatially offset relative to the entry port 302 and the exit port 306 such that there is no direct line-of-sight between the entry port 302 and the exit port 306 that also passes through the examination region 314. By way of example, a linear line 616 extending from a portion of the entry port 302 spatially nearest the examination region 314 in the y-direction to a portion of the exit port 306 spatially nearest the examination region 314 in the y-direction does not intersect the examination region 314. Accordingly, no linear line arbitrarily drawn between the entry port 302 and the exit port 306 will intersect the examination region 314.

Figure 6:
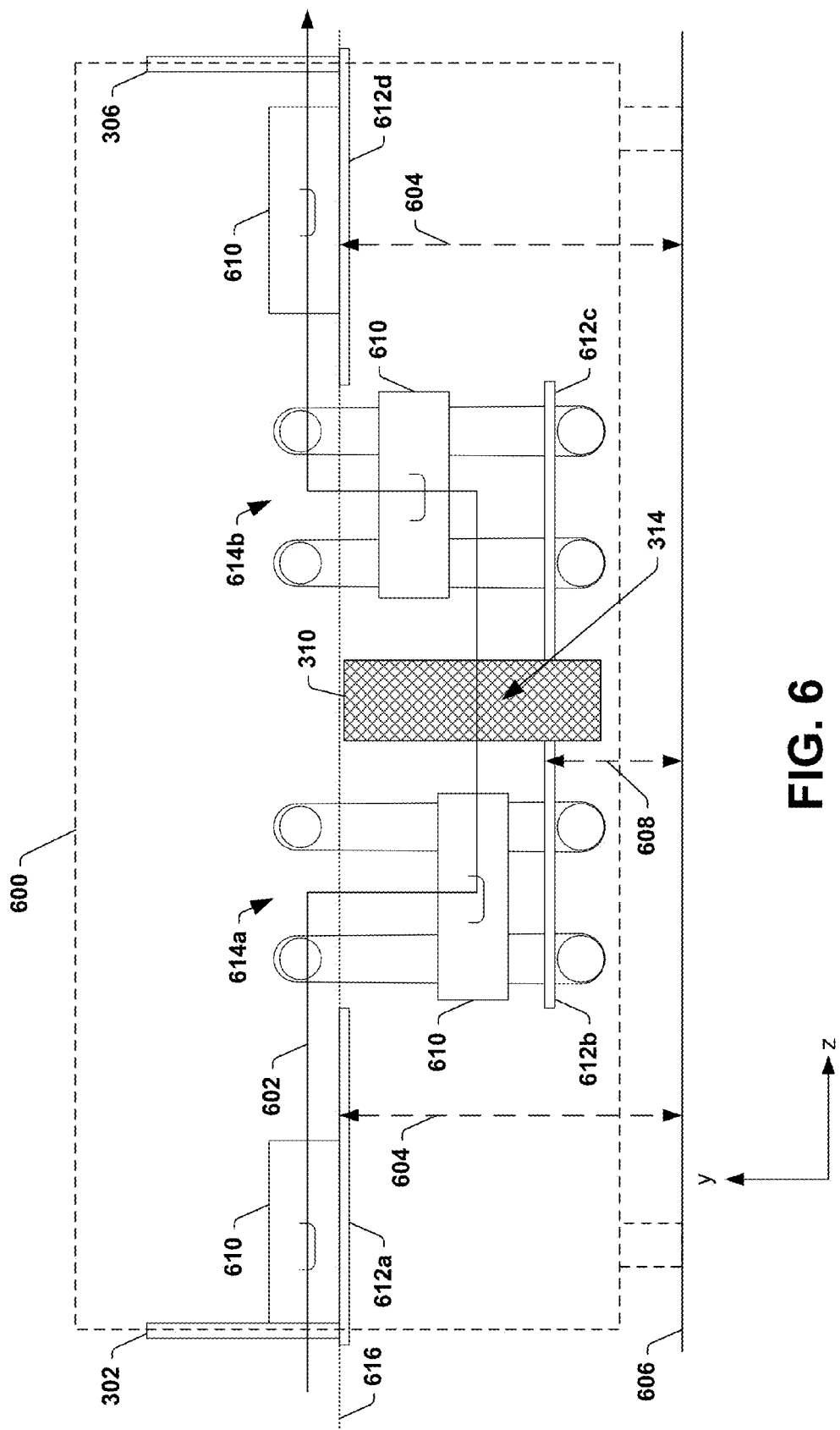
FIG. 6 illustrates an internal view of at least some of an example object scanner.

It may be appreciated that while FIG. 6 illustrates the entry port 302 and the exit port 306 as being located at a same elevation 604, in other embodiments, the entry port 302 may be at a different (e.g., greater or lesser) elevation than the exit port 306. For example, the entry port 302 may be positioned at an elevation that is greater than an elevation of the examination region 314 and the exit port 306 may be positioned at an elevation that is less than the elevation of the examination region 314 (e.g., such that the object 610 are translated in a downward stair-step fashion) between the entry port 302 and the exit port 306, for example. As another example, at least one of the entry port 302 or the exit port 306 may be positioned at a same (e.g., or different) elevation as the examination region 314.

Moreover, while the example layout illustrates substantially vertical changes in elevation between the entry port 302 and the examination region 314 and between the examination region 314 and the exit port 306, in some embodiments a portion of the path 602 between the entry port 302 and the examination region 314 and/or a portion of the path 602 between the examination region 314 and the exit port 306 may be substantially inclined (e.g., such that during a portion of the translation the object 610 is translated along a trajectory having both a z-component and a y-component).

Further, it may be appreciated that the foregoing layouts are merely example layouts and the instant application is not intended to be limited to such layouts. By way of example, while the example layouts provide for offsetting the examination region 314 in at least one of the x-direction or y-direction to such an extent that there is no direct line-of-sight between the entry port 302 and the exit port 306 that also passes through the examination region 314, other layouts may provide for merely a partially obstructed line-of-sight. By way of example, with respect to FIG. 6, the examination region 314 may be elevated slightly more such that the examination region 314 is partially within a line-of-sight between the entry port 302 and the exit port 306.

Figure 7:
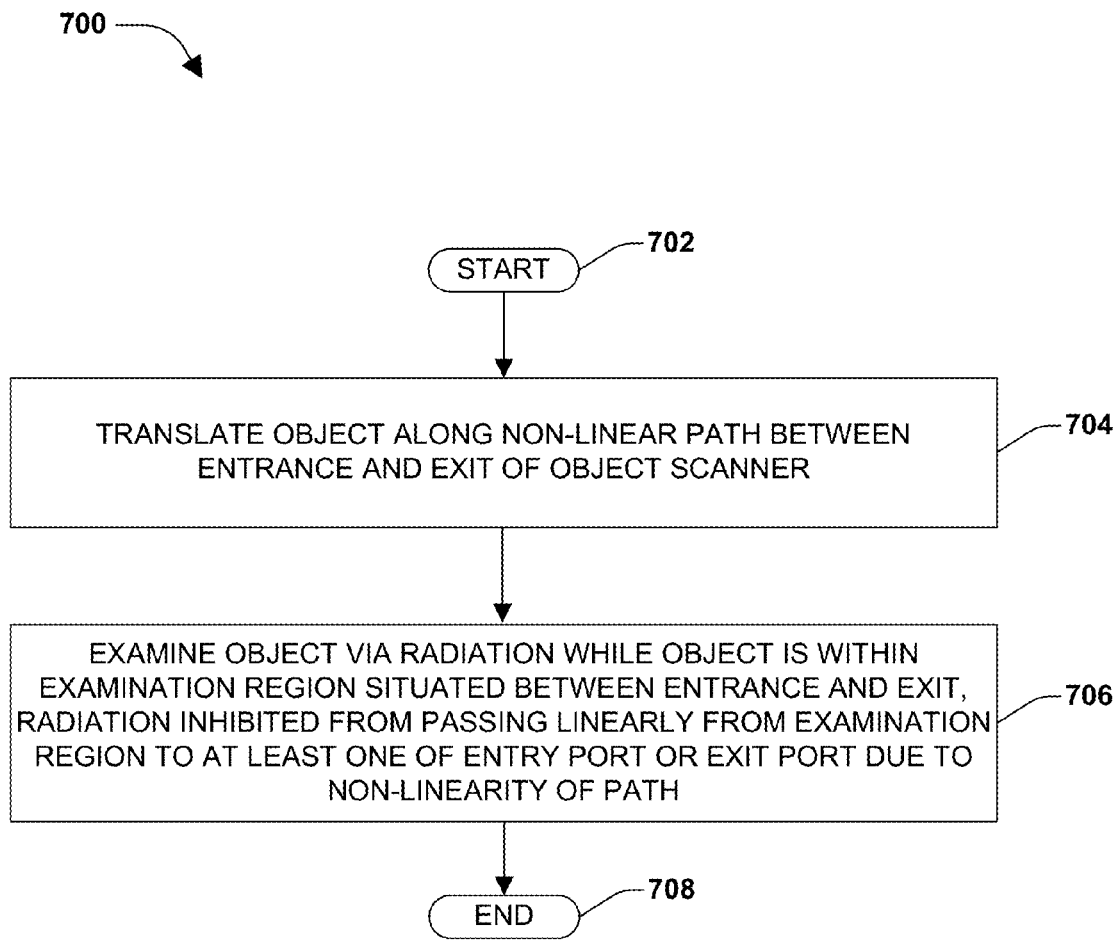
FIG. 7 is a flow chart diagram of an example method of examining an object.

Referring to FIG. 7, an example method 700 of examining an object via radiation is provided. The example method 700 begins at 702 and the object is translated along a non-linear path between the entry port and the exit port of an object scanner at 704. By way of example, as shown in FIGS. 3-6, an object may be at times translated along a trajectory parallel to a z-direction of the object scanner and at other times may be translated along a trajectory parallel to the x-direction and/or parallel to the y-direction. As another example, the object may be, at times, translated along a trajectory having a z-component and an x-component and/or having a z-component and a y-component, for example. In some embodiments, such as described with respect to FIG. 6, translating the object along a non-linear path comprises altering an elevation of the object relative to a floor of an examination room comprising the object scanner. In some other embodiments, such as described in FIGS. 3-5, translating the object along a non-linear path may comprise translating the object non-linearly within a plane substantially parallel to the plane of the floor. For example, the object may be translated in the z-direction for a first period of time and may be translated in the x-direction for a second period of time. As another example, the object may be translated in the z-direction for a first period of time and may be translated along a trajectory having both a z-component and an x-component for a second period of time, for example. In still other embodiments, such as described with respect to FIG. 5, the presence of an object at a specified location along the non-linear path, such as at an entry port of the object scanner may be detected (e.g., by a motion sensor or a position sensor) and a signal may be applied to trigger an actuator to reposition the object along the non-linear path, for example.

At 706 in the example method 700, the object is examined via radiation while the object is within an examination region situated between the entry port and the exit port, and radiation is inhibited from passing linearly from the examination region to at least one of the entry port or the exit port due the non-linearity of the path. By way of example, the non-linear path may be at least partially enclosed by one or more radiation attenuation walls (e.g., to form a tunnel) and, due to the non-linearity of the tunnel, there may be no linear path through which radiation can travel between the radiation source and the entry port and/or between the radiation source at the exit port.

At 708, the example method 700 ends.

Figure 8:
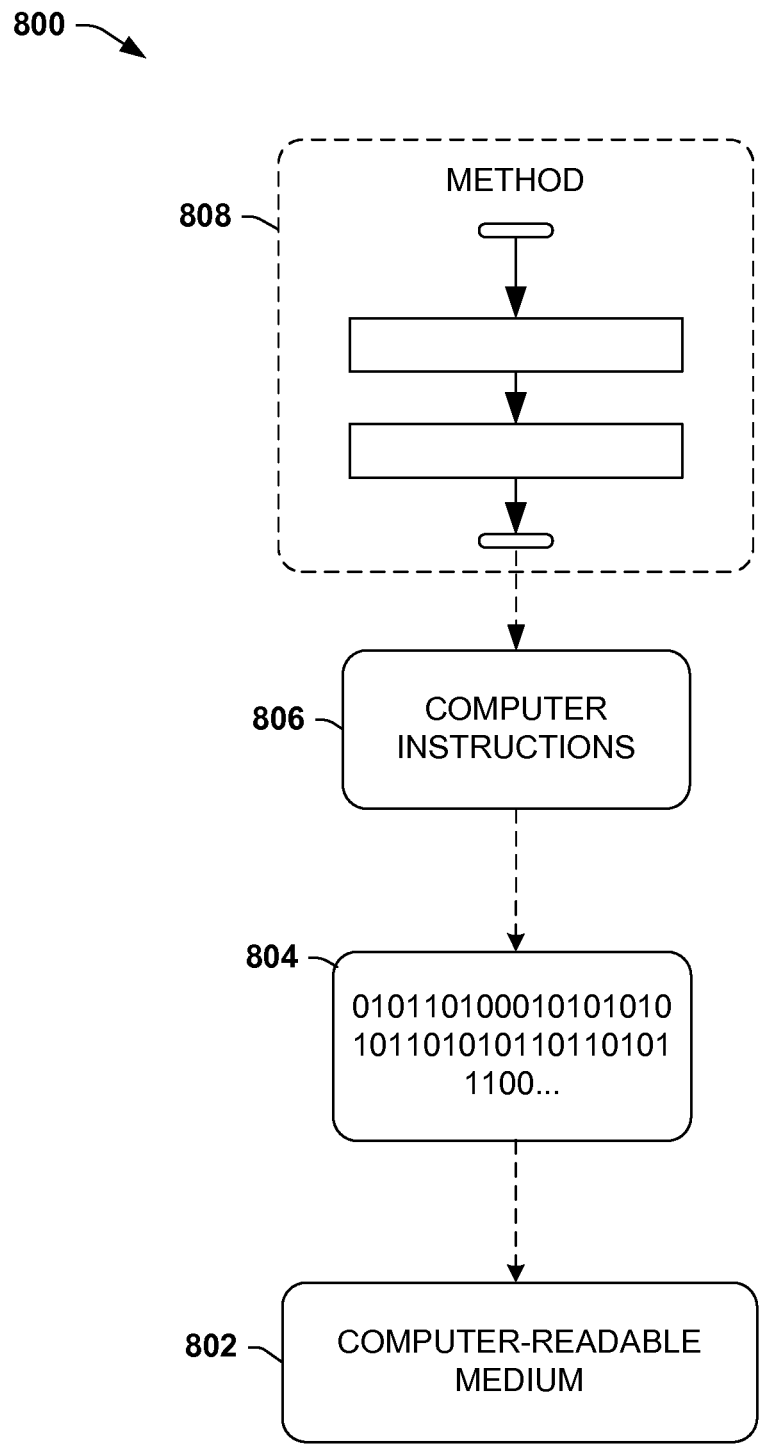
FIG. 8 is an illustration of an example computer-readable medium comprising processor-executable instructions wherein one or more of the provisions set forth herein may be embodied.

Still another embodiment involves a computer-readable medium comprising processor-executable instructions configured to implement one or more of the techniques presented herein. An example computer-readable medium (e.g., memory) that may be devised in these ways is illustrated in FIG. 8, wherein the implementation 800 comprises a computer-readable medium 802 (e.g., a flash drive, CD-R, DVD-R, application-specific integrated circuit (ASIC), field-programmable gate array (FPGA), a platter of a hard disk drive, etc.), on which is encoded computer-readable data 804. This computer-readable data 804 in turn comprises a set of processor-executable instructions 806 which when executed via a processing unit(s) is configured to operate according to one or more of the principles set forth herein. In some embodiments, the processor-executable instructions 806 may be configured to perform a method 808, such as at least some of the example method 700 of FIG. 7, for example. In other embodiments, the processor-executable instructions 806 may be configured to implement a system, such as at least some of the exemplary object scanner 100 of FIG. 1, at least some of the exemplary object scanner 200 of FIG. 2, at least some of the exemplary object scanner 300 of FIG. 3, at least some of the exemplary object scanner 400 of FIG. 4, at least some of the exemplary object scanner 500 of FIG. 5 and/or at least some of the exemplary object scanner 600 of FIG. 6, for example. Many such computer-readable media may be devised by those of ordinary skill in the art that are configured to operate in accordance with one or more of the techniques presented herein.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes", "having", "has", "with", or variants thereof are used in either the detailed description or the claims, such terms are intended to be inclusive in a manner similar to the term "comprising".

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used in this application, the terms "component," "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Further, unless specified otherwise, "first," "second," and/or the like are not intended to imply a temporal aspect, a spatial aspect, an ordering, etc. Rather, such terms are merely used as identifiers, names, etc. for features, elements, items, etc. (e.g., "a first channel and a second channel" generally corresponds to "channel A and channel B" or two different (or identical) channels or the same channel).

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application.

What is claimed is:

1. An object scanner configured to examine an object via ionizing radiation, the ionizing radiation comprising at least one of x-ray radiation or gamma radiation and the object scanner comprising:
  a first port through which the object at least one of enters or exits the object scanner;
  a rotating gantry configured to rotate at least one of an ionizing radiation source or a detector array about an axis of rotation, the rotating gantry defining a bore into which the object is situated during an examination of the object;
  a translator configured to translate the object along a non-linear path between the first port and the rotating gantry, wherein the rotating gantry is offset from the first port such that there is no line, parallel to the axis of rotation, that intersects the bore and the first port;

a first energy shield lying within a first plane and situated between the first port and the rotating gantry; and a second energy shield lying within a second plane and situated between the first port and the rotating gantry, the second plane not parallel to the first plane.

2. The object scanner of claim 1, comprising: a second port through which the object at least one of enters or exits the object scanner, wherein there is no linear line that intersects both the entry port and exit port and that also intersects the bore.

3. The object scanner of claim 2, comprising a housing extending between the first port and the second port and configured to substantially enclose the rotating gantry.

4. The object scanner of claim 1, the first energy shield comprising a first lead curtain.

5. The object scanner of claim 4, the second energy shield comprising a second lead curtain.

6. The object scanner of claim 1, the translator comprising a set of actuators and a plurality of rollers.

7. An object scanner configured to examine an object via ionizing radiation, the ionizing radiation comprising at least one of x-ray radiation or gamma radiation and the object scanner comprising:
   an entry port through which the object enters the object scanner;
   an exit port through which the object exits the object scanner;
   a rotating gantry configured to rotate at least one of an ionizing radiation source or a detector array, the rotating gantry defining a bore into which the object is disposed during an examination of the object, the rotating gantry situated between the entry port and the exit port, wherein there is no linear line that intersects both the entry port and exit port and that also intersects the bore;
   a translator configured to translate the object along a non-linear path between the entry port and the exit port;
   a first energy shield lying within a first plane and situated between the rotating gantry and the entry port or the exit port; and
   a second energy shield lying within a second plane and situated between the rotating gantry and the entry port or the exit port, the second plane not parallel to the first plane.

8. The object scanner of claim 7, the rotating gantry configured to rotate about an axis of rotation extending in a first direction and the rotating gantry spatially offset from at least one of the entry port or the exit port in a direction substantially perpendicular to the first direction.

9. The object scanner of claim 8, wherein there is no line, parallel to the axis of rotation, that intersects at least one of:
   the bore and the entry port; or
   the bore and the exit port.

10. The object scanner of claim 7, the first energy shield and the second enemy shield residing between the entry port and the rotating gantry.

11. The object scanner of claim 7, comprising a housing extending from the entry port to the exit port.

12. The object scanner of claim 7, the first energy shield and the second energy shield residing between the exit port and the rotating gantry.

13. The object scanner of claim 7, the translator comprising a first lift mechanism between the entry port and the rotating gantry, the first lift mechanism configured to alter an elevation of the object relative to a floor of an examination room comprising the object scanner.

14. The object scanner of claim 13, the translator comprising a second lift mechanism between the rotating gantry and the exit port, the second lift mechanism configured to alter the elevation of the object relative to the floor of the examination room.

15. The object scanner of claim 7, the translator comprising a series of rollers.

16. A method of examining an object, comprising:
   translating the object along a non-linear path between an entry port and an exit port of an object scanner, the translating comprising:
      translating the object through a first enemy shield lying within a first plane and situated between a rotating gantry and the entry port or the exit port; and
      translating the object through a second energy shield lying within a second plane and situated between the rotating gantry and the entry port or the exit port, the second plane not parallel to the first plane; and
   rotating, via the rotating gantry, at least one of an ionizing radiation source or a detector array, situated between the entry port and the exit port, relative to the object while emitting ionizing radiation from the ionizing radiation source to examine the object, the non-linear path inhibiting the ionizing radiation from passing linearly from an examination region, situated between the ionizing radiation source and the detector array, to at least one of the entry port or the exit port, the ionizing radiation comprising at least one of x-ray radiation or gamma radiation.

17. The method of claim 16, the translating comprising:
   altering an elevation of the object relative to a floor of an examination room comprising the object scanner.

18. The method of claim 16, the translating comprising:
   translating the object in a first direction for a first period of time; and
   translating the object in a second direction for a second period of time, the second direction substantially perpendicular to the first direction.

19. The method of claim 18, the first direction and the second direction laying within a plane substantially parallel to a plane of a floor of an examination room comprising the object scanner.

20. The method of claim 16, the translating comprising:
   detecting a presence of the object at a specified location along the non-linear path; and
   applying a signal to an actuator configured to reposition the object along the non-linear path.

\* \* \* \* \*